United States Patent
Iglesias Lores (10) Patent No.: US 8,877,811 B1
(45) Date of Patent: *Nov. 4, 2014

(54) HYPOGLYCEMIC ORAL DRUG FOR TREATING NON-INSULIN DEPENDENT AND INSULIN DEPENDENT DIABETES

(71) Applicant: Roberto Iglesias Lores, Cuidad Autonoma de Buenos Aires (AR)

(72) Inventor: Roberto Iglesias Lores, Cuidad Autonoma de Buenos Aires (AR)

(73) Assignee: CIP Kemicals, Corp., North Miami Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/903,246

(22) Filed: May 28, 2013

Related U.S. Application Data (63) Continuation-in-part of application No. 13/196,509, filed on Aug. 2, 2011, now Pat. No. 8,450,369.

(51) Int. Cl.
  *A61K 31/19* (2006.01)
  *C07C 53/00* (2006.01)

(52) U.S. Cl.
  USPC .......................................... 514/557; 562/512

(58) Field of Classification Search
  USPC .......................................... 562/512; 514/557
  See application file for complete search history.

(56) References Cited

U.S. PATENT DOCUMENTS 7,470,708 B2   12/2008   Moinet et al.
8,450,369 B1 *  5/2013   Lores ........................... 514/557

* cited by examiner

*Primary Examiner* — Rei-tsang Shiao
(74) *Attorney, Agent, or Firm* — Malloy & Malloy, P.L.

(57) ABSTRACT

The present invention is directed to novel diacid derivatives, pharmaceutical compositions comprising the diacid derivatives and methods for the treatment of insulin and non-insulin dependent diabetes mellitus and related disorders comprising administering to a subject in need thereof, the compounds of the present invention.

20 Claims, 2 Drawing Sheets

HYPOGLYCEMIC ORAL DRUG FOR TREATING NON-INSULIN DEPENDENT AND INSULIN DEPENDENT DIABETES

CLAIM OF PRIORITY

The present application is a "continuation-in-part" patent application of previously filed patent application having Ser. No. 13/196,509 filed on Aug. 2, 2011 which is set to issue on May 28, 2013 as U.S. Pat. No. 8,450,369.

BACKGROUND OF THE INVENTION

1. Field of the Invention

This invention relates to glycemic control compounds. More specifically, the invention relates to glycemic control compounds and methods of treating non-insulin dependent and insulin dependent diabetes with the compounds provided herein.

2. Description of the Related Art

Insulin-Dependent Diabetes Mellitus (IDDM), also known as diabetes mellitus type I, is an autoimmune disease that results in destruction of insulin-producing beta cells of the pancreas. Lack of insulin causes an increase of fasting blood glucose (around 70-120 mg/dL in non-diabetic people) that begins to appear in the urine above the renal threshold (about 190-200 mg/dL in most people), thereby resulting in the symptom with which the disease was identified in antiquity, sweet urine. Glycosuria, or glucose in the urine, causes patients to urinate more frequently and drink more than normal (polydipsia). These were the classic characteristic symptoms which prompted discovery of the disease.

Type I diabetes is lethal unless treated with exogenous insulin. Injection is the traditional, and still most common, method for administering insulin. Jet injection, indwelling catheters, and inhaled insulin have also been available at various times and there are several experimental methods as well.

Insulin resistance is a classic feature of many human disease conditions, such as in another type of diabetes, Non-Insulin-Dependent Diabetes Mellitus (NIDDM); obesity; hypertension; aging; etc. Diabetes mellitus is a disorder of carbohydrate metabolism, characterized by hyperglycemia and glycosuria resulting from inadequate production or utilization of insulin. NIDDM is a form of diabetes where utilization of insulin is inadequate. It occurs predominantly in adults, where adequate production of insulin is available for use, yet a defect exists in insulin-mediated utilization and metabolism of glucose and peripheral tissues. For some people with diabetes, a mutation in the gene(s) coding for insulin, for insulin receptor and/or for insulin-mediated signal transduction factor(s) leads to ineffective insulin and/or insulin-mediated effects, impairing the utilization or metabolism of glucose.

Diabetes mellitus is a disease affecting approximately 7.5 million people in the United States. The underlying cause of this disease is diminished or absent insulin production by the islets of Langerhans in the pancreas. Of the 7.5 million diagnosed diabetics in the United States, approximately one-third are treated using insulin replacement therapy. Those patients receiving insulin typically self-administer one or more doses of the drug per day by subcutaneous injection. Insulin is a polypeptide with a nominal molecular weight of 6,000 Daltons. Insulin has traditionally been produced by processing pig and cow pancreas to allow isolation of the natural product. More recently, recombinant technology has made it possible to produce human insulin in vitro. It is currently the common practice in the United States to institute the use of recombinant human insulin in all patients beginning insulin therapy.

Diabetes mellitus often develops from certain at risk populations; it is known that one such population are individuals with impaired glucose tolerance (IGT). The usual meaning of impaired glucose tolerance is that it is a condition intermediate between non-insulin-dependent diabetes mellitus and normal glucose tolerance. IGT is diagnosed by a procedure wherein an affected person's postprandial glucose response is determined to be abnormal as assessed by postprandial plasma glucose levels. In this test, a measured amount of glucose is given to the patient and blood glucose level measured at regular intervals, usually every ½ hour for the first two hours and every hour thereafter. In a "normal," or non-IGT individual, glucose levels rise during the first two hours to a level less than 140 mg/dl and then drop rapidly. In an impaired individual (IGT), the blood glucose levels are higher and the drop-off level is at a slower rate. A high percentage of the impaired (IGT) population is known to progress to non-insulin dependent diabetes mellitus.

The pathophysiology of non-insulin-dependent diabetes mellitus (NIDDM) consists of three major components: (1) peripheral insulin resistance, (2) increased hepatic glucose production, and (3) impaired insulin secretion. Intense research has been devoted to each of these areas, independently, in order to determine which abnormality is primary and which are secondary. The prevailing view is that a rational therapeutic pharmacological approach should involve intervention in insulin resistance to improve glucose homeostasis. As a result of the focus on individual abnormalities, several model therapies were developed to regulate glucose homeostasis in Type II diabetic patients.

The goal of diabetes therapy today is to achieve and maintain as near normal glycemia as possible to prevent the long-term microvascular and macrovascular complications of an elevated blood glucose.

One such therapy utilizes sulfonyl ureas to target one mechanism of hyperglycemia by augmenting insulin secretion from the beta cells. Since 1995, three new classes of agents have been added to the anti-diabetes armamentarium for the management of hyperglycemia. Metformin, a biguanide, targets additional mechanisms of hyperglycemia by inhibiting hepatic glucose production and enhancing peripheral glucose uptake and thereby reduce insulin resistance; thiazolidinediones, such as troglitazone, rosiglitazone and pioglitazone, decrease peripheral insulin resistance; and alpha-glucosidase inhibitors, such as acarbose and mioglitol, help control postprandial glucose excursion by delaying absorption of dietary carbohydrate. These agents are all indicated as monotherapy, and some are indicated for use in combination therapy, generally, after monotherapy has been found to be inadequate; yet, many side effects exist in the currently available oral agents.

To this end, there is a need for an orally administered agent for IDDM and NIDDM that can be substituted for the currently available therapies with better results and less side effects and toxicity.

SUMMARY OF THE INVENTION

The present invention relates to novel diacid compounds and their salts and the treatment of non-insulin dependent and insulin dependent diabetes in subjects in need thereof.

In one embodiment, the present invention provides diacid compounds, or salts thereof, that comprise a disubstituted double bond. The disubstitution consists of OH, Cl, and combinations thereof. In another embodiment, the compounds, or salts thereof, comprise substituted acids. The substitution consists of OH, COH, ethyl esters, methyl esters, and combinations thereof.

In some embodiments, the present invention provides the compound of Formula (I):

(I)

or a pharmaceutically acceptable salt thereof. In Formula (I), $R_1$ and $R_2$ are independently Cl or OH.

Figure 1:
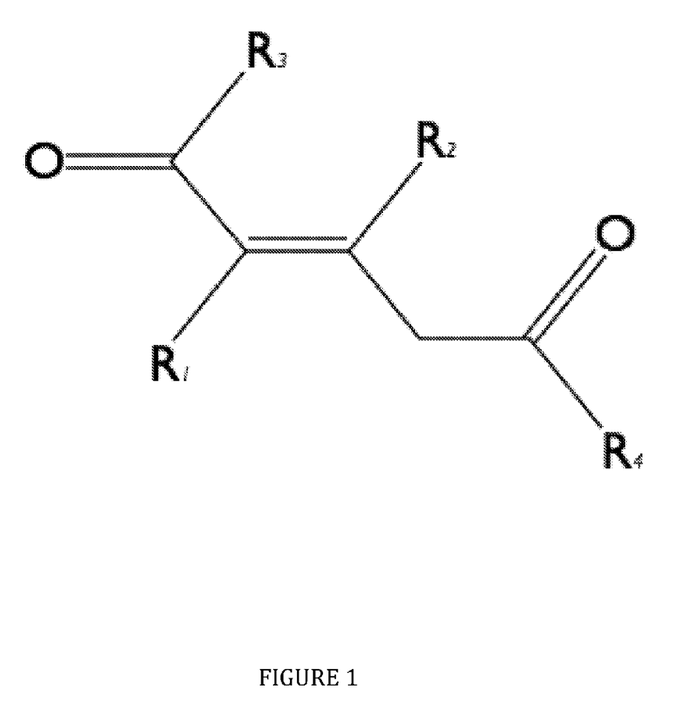
FIG. 1 is a depiction of Formula (II). In Formula (II), $R_1$ and $R_2$ are independently Cl or OH; $R_3$ is selected from the group consisting of —C—OH and —O—$R_5$, wherein $R_5$ is further selected from the group consisting of $C_2H_5$, $CH_3$ and H; and $R_4$ is selected from the group consisting of —C—OH and —O—$R_6$, wherein $R_6$ is further selected from the group consisting of $C_2H_5$, $CH_3$ and H.

In some embodiments, the present invention provides the compound of Formula (II):

(II)

or a pharmaceutically acceptable salt thereof. In Formula (II), $R_1$ and $R_2$ are independently Cl or OH; $R_3$ is selected from the group consisting of —C—OH and —O—$R_5$, wherein $R_5$ is further selected from the group consisting of $C_2H_5$, $CH_3$ and H; and $R_4$ is selected from the group consisting of —C—OH and —O—$R_6$, wherein $R_6$ is further selected from the group consisting of $C_2H_5$, $CH_3$ and H.

The present invention also provides pharmaceutical compositions comprising a therapeutically effective amount of the compound of Formula (I) or Formula (II) described herein.

The present invention also provides a method for the treatment of hyperglycemia in a subject comprising administering a therapeutically effective amount of the compound of Formula (I) or Formula (II) to the subject.

The present invention also provides a method for the treatment of non-insulin dependent or insulin dependent diabetes in a subject, comprising administering a therapeutically effective amount of the compound of Formula (I) or Formula (II) to the subject.

The present invention also provides a method for reducing insulin resistance in a subject comprising administering a therapeutically effective amount of the compound of Formula (I) or Formula (II) to the subject.

The present invention can also be provided in the form of kits of parts.

The methods, compositions and kits herein described can be used in connection with pharmaceutical, medical, and veterinary applications, as well as fundamental biological research and methodologies, as would be identifiable by a skilled person upon reading of the present disclosure. These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying figures in which.

DETAILED DESCRIPTION OF THE INVENTION

Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art.

The terminology used herein is for the purpose of describing particular embodiments only and is not intended to be limiting of the invention. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

Figure 2:
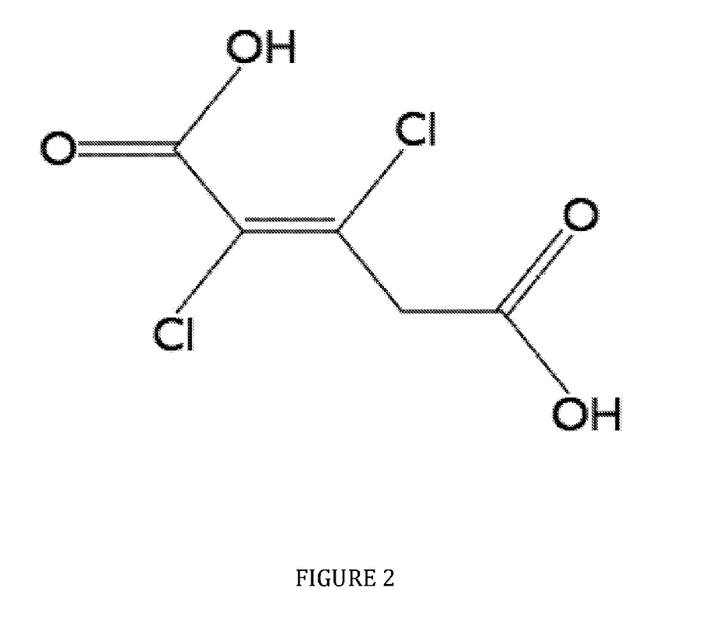
FIG. 2 is a schematic depiction of a preferred embodiment of the present invention, namely (2E)-2,3-dichloropent-2-enedioic acid.

(2E)-2,3-dichloropent-2-enedioic acid shall mean:

(2E)-2,3-hydroxypent-2-enedioic acid shall mean:

(2E)-2-chloro-3-hydroxypent-2-enedioic acid shall mean:

As used herein, the term "compound" refers to a compound of Formula (II), or its pharmaceutically acceptable salts or derivatives, unless clearly indicated otherwise. In Formula (II), $R_1$ and $R_2$ are independently Cl or OH; $R_3$ is selected from the group consisting of —C—OH and —O—$R_5$, wherein $R_5$ is further selected from the group consisting of $C_2H_5$, $CH_3$ and H; and $R_4$ is selected from the group consisting of —C—OH and —O—$R_6$, wherein $R_6$ is further selected from the group consisting of $C_2H_5$, $CH_3$ and H. The compounds of Formula (II) can be represented, described, and/or applied for the purposes of the present invention in its pharmaceutically acceptable salt form as well. The compound, its salts, and derivatives may be hydrated or anhydrous. Further, "compound" may refer to the chemical present in any state of matter, such as, but not limited to, a solid, such as crystallized or powdered; or as a liquid, such as dissolved, disassociated, or solubilized in an appropriate solvent. As used herein, "compound" may also refer to the chemical and any associated ions, molecules, or atoms.

As used herein, the term "derivative" refers to a chemical substance related structurally to another, i.e., an "original" substance, which can be referred to as a "parent" compound.

The compounds of Formula (II) can be an isolated compound and/or a synthetic compound. In some embodiments, the compounds of the present invention are isolated and purified from the flowering plant species *Petiveria alliacea*. In some embodiments, the compounds of the present invention are synthesized from various starting reactants and intermediates.

An "isolated compound" refers to a compound that is separated from the environment in which it may be normally present or that is enriched from a natural source. For example, a compound may be separated from nature to produce an isolated compound.

A "synthetic compound" or "synthesized compound" refers to a compound that is synthesized or derived by the purposeful execution of one or more chemical and/or physical reactions/manipulations of reagents and/or reactants to produce a product(s) or intermediate(s), and may be performed in an artificial setting, such as in a laboratory.

The term "pharmaceutically acceptable derivative" is any pharmaceutically acceptable salt, ester, salt of an ester, alcohol, diol, ether, aldehyde, ketone, carboxylic acid, or enol of a compound that can be made from the compound by a chemical or physical process. By way of example only, a derivative may be a structural analogue or orthologue and/or functional analogue that, upon administration to a subject, is capable of providing (directly or indirectly) the desired compound.

It should be understood that the compounds described herein are not to be limited to any particular stereochemical rendering, and include all stereochemical configurations. For example, the compounds of the present invention may contain one or more asymmetric centers or a non-aromatic double bond. Therefore, they can occur as racemates and racemic mixtures, single enantiomers, individual diastereomers, diastereomeric mixtures, and cis- or trans-isomeric forms. The compounds can also be dextrorotary (D) or levorotary (L). Moreover, each chiral center may be (S)- or (R)-. As such, it would be understood by those skilled in the art that the various forms of the compounds of the present invention would be encompassed by the present invention.

As used herein, the terms "composition" and "pharmaceutical composition" can be used interchangeably and refer broadly to any combination of materials containing a compound described herein. The composition may comprise an aqueous solution or a dry formulation. Furthermore, the composition may be in a sterile form. The compositions described herein may also be stored in a freeze-dried form and may be associated with stabilizing agents. As a dry formulation, the composition may further comprise other compounds, excipients, fillers, carriers (vehicles), and binders including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Specifically, whether an aqueous solution or a dry formulation, pharmaceutically acceptable carriers, excipients and binders contemplated for use in the practice of the present invention are those that are compatible with the active ingredient (i.e., active compound) and which render the compounds of the invention amenable to delivery, such as intravenous delivery, subcutaneous delivery, transcutaneous delivery, intracutaneous delivery, oral delivery, and the like; and bioavailability.

The term "substituted," as used herein, refers to a group as defined above in which one or more bonds to a carbon, oxygen or hydrogen atom contained therein are broken and new bonds are formed to atoms such as, but not limited to, a halogen atom, such as Cl; an oxygen atom in groups such as hydroxyl groups, methyl ester groups, and ethyl ester groups; and a carbon atom, such as in carboxylic acid groups.

The phrases "pharmaceutically acceptable salt" and "salt," as used herein, refer to the salts of the compounds of this invention that are non-toxic. Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as, but not limited to, hydrochloric acid, citric acid, benzoic acid, sulfuric acid, acetic acid, maleic acid, succinic acid, tartaric acid, carbonic acid, fumaric acid, or phosphoric acid. Furthermore, where the compounds of the invention carry an acidic moiety, suitable pharmaceutically acceptable salts thereof may include salts formed with suitable organic ligands, e.g., quaternary ammonium salts; alkali metal salts, e.g., sodium or potassium salts; and alkaline earth metal salts, e.g., calcium or magnesium salts. Therefore, representative pharmaceutically acceptable salts include, but are not limited to, the following: acetate, benzenesulfonate, benzoate, bicarbonate, bisulfate, carbonate, chloride, palmitate, citrate, dihydrochloride, glutamate, tartrate, teoclate, tosylate, glycollylarsanilate, hexylresorcinate, hydrabamine, hydrobromide, iodide, methylnitrate, methylsulfate, mucate, napsylate, nitrate, N-methylglucamine ammonium salt, oleate, pamoate, pantothenate, edetate, edisylate, estolate, lactate, esylate, fumarate, gluceptate, hydrochloride, hydroxynaphthoate, mandelate, mesylate, bromide, calcium edetate, camsylate, subacetate, succinate, tannate, gluconate, phosphate/diphosphate, isothionate, lactobionate, laurate, malate, maleate, methylbromide, clavulanate, polygalacturonate, salicylate, stearate, sulfate, bitartrate, borate, triethiodide and valerate. Representative acids and bases which may be used in the preparation of pharmaceutically acceptable salts include, but are not limited to, the following: acids including acetic acid, ascorbic acid, L-aspartic acid, 2,2-dichloroacetic acid, acylated amino acids, adipic acid, alginic acid, (+)-(1S)-camphorsulfonic acid, capric acid, caproic acid, ethane-sulfonic acid, 2-hydroxy-ethanesulfonic acid, formic acid, caprylic acid, cinnamic acid, citric acid, cyclamic acid, dodecylsulfuric acid, ethane-1,2-disulfonic acid, fumaric acid, galactaric acid, benzenesulfonic acid, benzoic acid, 4-acetamidobenzoic acid, (+)-camphoric acid, camphorsulfonic acid, gentisic acid, glucoheptonic acid, D-gluconic acid, D-glucuronic acid, L-glutamic acid, a-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxynaphthoic acid, nicotine acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, magnesium hydroxide, 4-(2-hydroxyethyl)morpholine, piperazine, potassium hydroxide, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-arginine, benethamine, benzathine, L-lysine, 1-(2-hydroxyethyl)-pyrrolidine, secondary amine, tromethamine, sodium hydroxide, triethanolamine, and zinc hydroxide.

As used herein, the term "subject" refers to any animal (e.g., mammals, birds, reptiles, amphibians, fish), including, but not limited to, humans, non-human primates, rodents, and the like, which is to be the recipient of a particular treatment. Typically, the terms "subject" and "patient" may be used interchangeably herein in reference to a subject. Furthermore, transgenic animals (e.g., transgenic rats and mice) are useful in the methods of the present invention.

As used herein, the term "administering" refers to providing or delivering a therapeutically effective amount of a chemical compound or pharmaceutical composition to a subject, using intravenous, subcutaneous, transcutaneous, intracutaneous, oral, and the like administration. The chemical compound of the present invention can be administered alone, but may be administered with other pharmaceutically acceptable compounds, excipients, fillers, binders, or carriers (vehicles) selected based upon the chosen route of administration and standard pharmaceutical practice. Administration may be by way of carriers or vehicles, such as injectable solutions, including sterile aqueous or non-aqueous solutions, or saline solutions; capsules; tablets; granules; pellets; powders; suspensions or emulsions or microemulsions; patches; micelles; liposomes; vesicles; implants, including microimplants; synthetic polymers; microspheres; nanoparticles; and the like.

The terms "effective amount" and "therapeutically effective amount" may be used interchangeably, and as applied to the compounds and pharmaceutical compositions herein, mean the quantity necessary to affect the desired therapeutic result. For example, an effective amount is a level effective to treat, cure, or alleviate the symptoms of a disorder for which the therapeutic compound or composition is being administered. Amounts effective for the particular therapeutic goal sought will depend upon a variety of factors including the disorder being treated and its severity; the activity of the specific compound or pharmaceutical composition used; the route of administration; the rate of clearance of the specific compound; the duration of treatment; treatment regimen; the drugs used in combination or coincident with the specific compound or composition; the age, body weight, sex, diet, physiology and general health of the subject being treated; and like factors well known to one of skill in the relevant scientific art. Some variation in dosage will necessarily occur depending upon the condition of the subject being treated, and the physician will, in any event, determine the appropriate dose for the individual subject, e.g., patient. In some embodiments of the present invention, an "effective amount" is about 5 mg/kg to about 25 mg/kg.

As used herein, "disorder" refers to a disorder, disease or condition, and the terms can be used interchangeably. The terms would refer to any condition that impairs normal function. In embodiments of the present invention, the disorder includes, but is not limited to, insulin and non-insulin dependent diabetes mellitus, hyperglycemia, hypoglycemia, glycosuria, and insulin resistance. The condition may be caused by sporadic or inherited genetic abnormalities. The condition may also be caused by non-genetic abnormalities. For instance, the condition may be caused by environmental factors, such as the subject's diet (e.g., glucose intake); weight (i.e., obesity); or additional diseases that exacerbate or aid in onset of the disorder.

The terms "non-insulin dependent diabetes mellitus (NIDDM)," "non-insulin dependent diabetes," "type 2 diabetes," "type II diabetes," and "type II diabetes mellitus" are used interchangeably herein, and refer to a chronic disorder characterized by insulin resistance at the level of fat and muscle cells and resultant hyperglycemia.

The terms "insulin dependent diabetes mellitus (IDDM)," "insulin dependent diabetes," "type 1 diabetes," "type I diabetes," and "type I diabetes mellitus" are used interchangeably herein, and refer to a chronic disorder characterized by autoimmune destruction of insulin-producing beta cells of the pancreas and resultant increase in blood and urine glucose.

As used herein, "treatment" or "treating" refers to arresting or inhibiting, or attempting to arrest or inhibit, the development or progression of a disorder and/or causing, or attempting to cause, the reduction, suppression, regression, or remission of a disorder. As would be understood by those skilled in the art, various clinical and scientific methodologies and assays may be used to assess the development or progression of a disorder, and similarly, various clinical and scientific methodologies and assays may be used to assess the reduction, regression, or remission of a disorder. Similarly, in the case of insulin and non-insulin dependent diabetes mellitus, "treatment" refers both to treating subjects diagnosed with insulin or non-insulin dependent diabetes mellitus and those at risk of developing insulin or non-insulin dependent diabetes mellitus.

Compounds of the Present Invention

Compounds useful in the present invention are represented by Formula (I):

(I)

In compounds of Formula (I), $R_1$ and $R_2$ are independently Cl or OH. For example, in some embodiments of compounds of Formula (I), $R_1$ is Cl. In other embodiments of compounds of Formula (I), $R_1$ is OH. Similarly, in some embodiments of compounds of Formula (I), $R_2$ is Cl. In other embodiments of compounds of Formula (I), $R_2$ is OH. As would be understood by those skilled in the art, "Cl" represents chlorine, and "OH" represents hydroxide or the hydroxide ion or the hydroxyl group. In some embodiments, the pharmaceutically acceptable salt of Formula (I) is useful in the present invention.

Compounds useful in the present invention are represented by Formula (II):

(II)

In compounds of Formula (II), $R_2$ is selected from the group consisting of Cl and OH. In some embodiments of compounds of Formula (II), $R_1$ is Cl. In other embodiments of compounds of Formula (II), $R_2$ is OH.

In compounds of Formula (II), $R_2$ is selected from the group consisting of Cl and OH. In some embodiments of compounds of Formula (II), $R_2$ is Cl. In other embodiments of compounds of Formula (II), $R_2$ is OH.

In compounds of Formula (II), $R_3$ is selected from the group consisting of —C—OH and —O—$R_5$. $R_5$ is further selected from the group consisting of $C_2H_5$, $CH_3$ and H. In some embodiments of compounds of Formula (II), $R_5$ is $C_2H_5$ such that $R_3$ is an ethyl ester. In some embodiments of compounds of Formula (II), $R_5$ is $CH_3$ such that $R_3$ is a methyl ester. In some embodiments of compounds of Formula (II), $R_5$ is H, i.e., hydrogen, such that $R_3$ forms a carboxylic acid group, or COOH. In other embodiments, $R_3$ is —C—OH, such that $R_3$ forms a methyl alcohol group.

In compounds of Formula (II), $R_4$ is selected from the group consisting of —C—OH and —O—$R_6$. $R_6$ is further selected from the group consisting of $C_2H_5$, $CH_3$ and H. In some embodiments of compounds of Formula (II), $R_6$ is $C_2H_5$ such that $R_4$ is an ethyl ester. In some embodiments of compounds of Formula (II), $R_6$ is $CH_3$ such that $R_4$ is a methyl ester. In some embodiments of compounds of Formula (II), $R_6$ is H, i.e., hydrogen, such that $R_4$ forms a carboxylic acid group, or COOH. In other embodiments, $R_4$ is —C—OH, such that $R_4$ forms a methyl alcohol group.

In a preferred embodiment of the present invention, the compound is (2E)-2,3-dichloropent-2-enedioic acid, which is represented by Formula (III):

(III)

In one embodiment of the present invention, the compound is (2E)-2,3-hydroxypent-2-enedioic acid, which is represented by Formula (IV):

(IV)

In one embodiment of the present invention, the compound is (2E)-2-chloro-3-hydroxypent-2-enedioic acid, which is represented by Formula (V):

(V)

The present invention is meant to cover all compounds discussed, regardless of absolute configurations and/or stereochemical considerations.

Possible Therapeutic Uses of the Compounds of the Present Invention

In accordance with the invention, the compounds described herein are administered to a subject in need of treatment or prevention of a condition, such as hyperglycemia. In some embodiments, the side effects of the administration of the compounds of the present invention are reduced in kidneys and/or liver.

The present invention is directed to a method for the treatment of hyperglycemia in a subject in need thereof comprising administering a therapeutically effective amount of a compound of Formula (II) to the subject. In some embodiments, the therapeutically effective amount is in the range of about 5 mg/kg to about 25 mg/kg. It should be understood, however, that amounts above 25 mg/kg and below 5 mg/kg may also be used depending on the treatment desired and the type of subject (i.e. rat, human, dog, etc.) being treated. Moreover, the compound may be administered alone or as a pharmaceutical composition.

In accordance with at least one embodiment of the present invention, a method for the treatment of hyperglycemia in a subject in need thereof comprises administering a therapeutically effective amount of a compound of Formula (III) to the subject. In some embodiments, the compound of Formula (III) is (2E)-2,3-dichloropent-2-enedioic acid. In some embodiments, the therapeutically effective amount is in the range of about 5 mg/kg to about 25 mg/kg. It should be understood, however, that amounts above 25 mg/kg and below 5 mg/kg may also be used depending on the treatment desired and the type of subject (i.e. rat, human, dog, etc.) being treated. Moreover, the compound may be administered alone or as a pharmaceutical composition.

In accordance with at least another embodiment of the present invention, a method for the treatment of hyperglycemia in a subject in need thereof comprises administering a therapeutically effective amount of a compound of Formula (IV) to the subject. In some embodiments, the compound of Formula (IV) is (2E)-2,3-hydroxypent-2-enedioic acid. In some embodiments, the therapeutically effective amount is in the range of about 5 mg/kg to about 25 mg/kg. It should be understood, however, that amounts above 25 mg/kg and below 5 mg/kg may also be used depending on the treatment desired and the type of subject (i.e. rat, human, dog, etc.) being treated. Moreover, the compound may be administered alone or as a pharmaceutical composition.

The present invention is also directed to a method for the treatment of non-insulin dependent or insulin dependent diabetes in a subject in need thereof comprising administering a therapeutically effective amount of a compound of Formula (II) to the subject. In some embodiments, the therapeutically effective amount is in the range of about 5 mg/kg to about 25 mg/kg. It should be understood, however, that amounts above 25 mg/kg and below 5 mg/kg may also be used depending on the treatment desired and the type of subject (i.e. rat, human, dog, etc.) being treated. Moreover, the compound may be administered alone or as a pharmaceutical composition.

In accordance with at least one embodiment of the present invention, a method for the treatment of non-insulin dependent or insulin dependent diabetes in a subject in need thereof comprises administering a therapeutically effective amount of a compound of Formula (III) to the subject. In some embodiments, the compound of Formula (III) is (2E)-2,3-dichloropent-2-enedioic acid. In some embodiments, the therapeutically effective amount is in the range of about 5 mg/kg to about 25 mg/kg. It should be understood, however, that amounts above 25 mg/kg and below 5 mg/kg may also be used depending on the treatment desired and the type of subject (i.e. rat, human, dog, etc.) being treated. Moreover, the compound may be administered alone or as a pharmaceutical composition.

In accordance with at least another embodiment of the present invention, a method for the treatment of non-insulin dependent or insulin dependent diabetes in a subject in need thereof comprises administering a therapeutically effective amount of a compound of Formula (IV) to the subject. In some embodiments, the compound of Formula (IV) is (2E)-2,3-hydroxypent-2-enedioic acid. In some embodiments, the therapeutically effective amount is in the range of about 5 mg/kg to about 25 mg/kg. It should be understood, however, that amounts above 25 mg/kg and below 5 mg/kg may also be used depending on the treatment desired and the type of subject (i.e. rat, human, dog, etc.) being treated. Moreover, the compound may be administered alone or as a pharmaceutical composition.

The present invention is also directed to a method for reducing insulin resistance in a subject in need thereof comprising administering a therapeutically effective amount of a compound of Formula (II) to the subject. In some embodiments, the therapeutically effective amount is in the range of about 5 mg/kg to about 25 mg/kg. It should be understood, however, that amounts above 25 mg/kg and below 5 mg/kg may also be used depending on the treatment desired and the type of subject (i.e. rat, human, dog, etc.) being treated. Moreover, the compound may be administered alone or as a pharmaceutical composition.

In accordance with at least one embodiment of the present invention, a method for reducing insulin resistance in a subject in need thereof comprises administering a therapeutically effective amount of a compound of Formula (III) to the subject. In some embodiments, the compound of Formula (III) is (2E)-2,3-dichloropent-2-enedioic acid. In some embodiments, the therapeutically effective amount is in the range of about 5 mg/kg to about 25 mg/kg of (2E)-2,3-dichloropent-2-enedioic acid. It should be understood, however, that amounts above 25 mg/kg and below 5 mg/kg may also be used depending on the treatment desired and the type of subject (i.e. rat, human, dog, etc.) being treated.

In accordance with at least another embodiment of the present invention, a method for reducing insulin resistance in a subject in need thereof comprises administering a therapeutically effective amount of a compound of Formula (IV) to the subject. In some embodiments, the compound of Formula (IV) is (2E)-2,3-hydroxypent-2-enedioic acid. In some embodiments, the therapeutically effective amount is in the range of about 5 mg/kg to about 25 mg/kg of (2E)-2,3-dichloropent-2-enedioic acid. It should be understood, however, that amounts above 25 mg/kg and below 5 mg/kg may also be used depending on the treatment desired and the type of subject (i.e. rat, human, dog, etc.) being treated.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Anyone or more of the features of the previously described embodiments can be combined in any manner with one or more features of any other embodiments in the present invention. Furthermore, many variations of the invention will become apparent to those skilled in the art upon review of the specification.

Those having skill in the art of chemical synthesis will recognize that the starting components and reaction conditions may be varied, the sequence of the reactions altered, and other additional steps used to produce compounds encompassed by the present invention.

All publications and patent documents cited in this application are incorporated by reference in pertinent part for all purposes to the same extent as if each individual publication or patent document were so individually denoted. By citation of various references in this document, Applicant does not admit any particular reference is "prior art" to their invention.

The synthesis of compounds of the present invention is illustrated by the following examples, which are not to be construed as limiting the invention in scope or spirit to the procedures and compounds described in them.

EXAMPLES

All reactions described in the Examples were performed at standard temperature and pressure, unless otherwise specified.

Example 1

Preparation of (2E)-2,3-dichloropent-2-enedioic acid, which is represented by Formula (III):

(III)

Part 1:

2-pentenedioic acid was dissolved in a solution of carbon tetrachloride (CCl$_4$) and bromine (Br$_2$) with stirring until the resulting solution turned red, indicating that the reaction was complete. The constituents of the reaction were in equal molar ratios. The solution is then heated to remove excess bromine from solution.

Part 2:

The resulting dibromide compound solution was then mixed with potassium hydroxide (KOH) dissolved in ethanol (EtOH) and refluxed for 30 minutes to obtain a 2,3-pentynedioic acid solution.

Part 3:

(III)

Chlorine (Cl$_2$) is added to the 2,3-pentynedioic acid solution in equal molar ratios to obtain the desired compound of Formula (III), (2E)-2,3-dichloropent-2-enedioic acid.

Example 2

Preparation of (2E)-2,3-hydroxypent-2-enedioic acid, which is represented by Formula (IV):

(IV)

Parts 1 and 2 are performed in a manner analogous to that set forth in Example 1.

Part 3:

(IV)

Water (H$_2$O) is added to the 2,3-pentynedioic acid solution in equal molar ratios to obtain the desired compound of Formula (IV), (2E)-2,3-hydroxypent-2-enedioic acid.

Example 3

Preparation of (2E)-2-chloro-3-hydroxypent-2-enedioic acid, which is represented by Formula (V):

(V)

Parts 1 and 2 are performed in a manner analogous to that set forth in Example 1.

Part 3:

(V)

-continued

Chlorine gas is bubbled through water and added to the 2,3-pentynedioic acid solution in equal molar ratios to obtain the desired compound of Formula (V), (2E)-2-chloro-3-hydroxypent-2-enedioic acid.

It is to be appreciated that the Detailed Description section, and not the Abstract section, is intended to be used to interpret the claims. The Abstract section may set forth one or more but not all exemplary embodiments of the present invention as contemplated by the inventor(s), and thus, are not intended to limit the present invention and the appended claims in any way.

The foregoing description of the specific embodiments should fully reveal the general nature of the invention so that others can, by applying knowledge within the skill of the art, readily modify and/or adapt for various applications such specific embodiments, without undue experimentation, without departing from the general concept of the present invention. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. Moreover, the breadth and scope of the present invention should not be limited by any of the above-described exemplary embodiments, but should similarly be defined only in accordance with the following claims and their equivalents.

What is claimed is:

1. A compound of Formula (I):

or a pharmaceutically acceptable salt thereof, wherein
$R_1$ consists of at least Cl or OH and $R_2$ consists of at least Cl or OH.

2. The compound of claim 1 wherein $R_1$ and $R_2$ are Cl.
3. The compound of claim 1 wherein $R_1$ and $R_2$ are OH.
4. The compound of claim 1 wherein $R_1$ is $C_1$ and $R_2$ is OH.
5. The compound of claim 1 wherein $R_1$ is OH and $R_2$ is Cl.
6. A compound of Formula (II):

or a pharmaceutically acceptable salt thereof, wherein
$R_1$ consists of at least Cl or OH and $R_2$ consists of at least Cl or OH;
$R_3$ is selected from the group consists of at least —C—OH and —O—$R_5$,
wherein $R_5$ is further selected from the group consists of at least $C_2H_5$, $CH_3$ and H; and
$R_4$ is selected from the group consists of at least —C—OH and —O—$R_6$,
wherein $R_6$ is further selected from the group consists of at least $C_2H_5$, $CH_3$ and H.

7. The compound of claim 6 wherein $R_1$ and $R_2$ are Cl.
8. The compound of claim 6 wherein $R_1$ and $R_2$ are OH.
9. The compound of claim 6 wherein $R_1$ is $C_1$ and $R_2$ is OH.
10. The compound of claim 6 wherein $R_1$ is OH and $R_2$ is Cl.
11. The compound of claim 6 wherein $R_3$ is OH.
12. The compound of claim 6 wherein $R_4$ is OH.
13. The compound of claim 7 wherein $R_3$ and $R_4$ are OH.
14. A pharmaceutical composition comprising a therapeutically effective amount of the compound of claim 1.
15. A pharmaceutical composition comprising a therapeutically effective amount of the compound of claim 6.
16. A method for the treatment of hyperglycemia in a subject comprising administering a therapeutically effective amount of the compound of claim 6 to the subject.
17. The method of claim 16 wherein the therapeutically effective amount is in the range of about 5 mg/kg to about 25 mg/kg.
18. A method for the treatment of non-insulin dependent or insulin dependent diabetes in a subject, comprising administering a therapeutically effective amount of the compound of claim 6 to the subject.
19. The method of claim 18 wherein the therapeutically effective amount is in the range of about 5 mg/kg to about 25 mg/kg.
20. A method for reducing insulin resistance in a subject comprising administering a therapeutically effective amount of the compound of claim 6 to the subject.

* * * * *